(12) United States Patent
Baumann et al.

(10) Patent No.: US 6,812,468 B1
(45) Date of Patent: Nov. 2, 2004

(54) THERMAL-WAVE MEASURING METHOD

(75) Inventors: Joachim Baumann, München (DE); Thomas Mangold, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/762,508

(22) PCT Filed: Aug. 18, 1999

(86) PCT No.: PCT/DE99/02590
§ 371 (c)(1), (2), (4) Date: Feb. 7, 2001

(87) PCT Pub. No.: WO00/11450
PCT Pub. Date: Mar. 2, 2000

(30) Foreign Application Priority Data

Aug. 20, 1998 (DE) .......................... 198 37 889

(51) Int. Cl.[7] .............................................. G01N 21/17
(52) U.S. Cl. .............................. 250/341.6; 250/341.7; 250/341.8
(58) Field of Search ......................... 250/341.6, 339.06, 250/341.1, 341.5, 341.7, 341.8, 358.1; 374/43, 44, 45

(56) References Cited

U.S. PATENT DOCUMENTS

| | | | | |
|---|---|---|---|---|
| 4,255,971 A | * | 3/1981 | Rosencwaig | ................. 356/432 |
| 4,513,384 A | | 4/1985 | Rosencwaig | |
| 4,874,251 A | * | 10/1989 | Thomas et al. | .............. 250/334 |
| 4,875,175 A | | 10/1989 | Egee et al. | |
| 5,206,710 A | | 4/1993 | Geiler et al. | |
| 5,408,327 A | * | 4/1995 | Geiler et al. | ................. 356/432 |
| 5,713,665 A | * | 2/1998 | Kato et al. | ...................... 374/43 |
| 5,760,400 A | * | 6/1998 | Prekel et al. | ............. 250/341.6 |
| 5,814,820 A | * | 9/1998 | Dong et al. | ............... 250/458.1 |
| 6,240,309 B1 | * | 5/2001 | Yamashita et al. | ........ 250/227.2 |

FOREIGN PATENT DOCUMENTS

| | | |
|---|---|---|
| DE | 36 31 652 | 3/1989 |
| DE | 40 35 266 | 5/1992 |
| DE | 42 03 272 A1 | 8/1993 |
| DE | 42 03 272 C2 | 5/1995 |
| DE | 195 20 788 | 7/1996 |
| DE | 196 46 947 | 5/1998 |
| EP | 0 233 120 | 8/1987 |
| EP | 0 735 378 | 10/1996 |

OTHER PUBLICATIONS

Wagner, M et al; "Single–beam thermowave analysis of ion implanted and laser annealed semiconductors", Measurement Science & Technology, (1991), vol. 2, No. 11, Bristol, GB, pp. 1088–1093.

Wagner, M. et al; "Nondestructive Measuring and Testing with Optically Excited Thermal Waves", Laser & Optoelektronik, (1994), vol. 26, No. 1, pp. 63–68.

* cited by examiner

*Primary Examiner*—Albert Gagliardi
(74) *Attorney, Agent, or Firm*—Harness, Dickey & Pierce, P.L.C.

(57) ABSTRACT

The simultaneous multi-frequency excitation with two or more discrete frequencies of an electrically modulatable hot light source enables the parallel evaluation corresponding to the different drive frequencies. As a result thereof, the measuring time in the measurement of multi-layer systems is significantly shortened. As a result of a suitable selection of the discrete frequency parts of the drive frequencies, these can be adapted to the measurement problem.

10 Claims, 5 Drawing Sheets

THERMAL-WAVE MEASURING METHOD

The invention is directed to a fast, contact-free, geometrical as well as thermal characterization of a planar multi-layer structure. Measurements with respect thereto are in demand, for example, in automotive multi-coat lacquering. The category of thermal wave measuring methods are known, for example, under the designations heat sources, photothermal and photoacoustic methods or lock-in thermography.

Methods that, for example, pass by the name "photothermal measuring methods, thermal wave measuring methods or lock-in thermography" belong to the Prior Art. Therein, a material to be tested and having a superficial layer structure is heated periodically and in regions with a heat source. The heating must be capable of being modulated, so that an amplitude modulation is present. The modulation frequencies of the heating can thus be sequentially tuned, and the photothermal signal that derives from a specimen is measured as a function of the frequency based on amplitude and, in particular, its phase. The evaluation in terms of two or more unknowns (for example, layer thicknesses) can thereby generally not be implemented in closed analytical form since an "inverse problem" is present here. This is equivalent to saying that the solving of the equation system for an unknown is not possible without further ado.

Disadvantages of the methods belonging to the Prior Art are comprised, for example, therein that the sequential tuning of the modulation frequency of the modulatable heat source lasts a long time.

The invention is based on the object of offering a thermal wave measuring method with which a significant speed-up of a corresponding measurement and evaluation can be achieved. A critical goal is comprised in the use of a fast thermal wave measuring method for monitoring layering structures in ongoing production.

This object is achieved by the feature combination of claim 1.

The invention is based on the perception that the heat source employed for the regional heating of a layer structure can be simultaneously driven with a plurality of different frequencies and the infrared radiation corresponding to the drive frequencies can be simultaneously evaluated. Thus, specific supporting points can be determined from a characteristic for the sequential tuning of the heat source over the frequency, a specific plurality of different, discrete frequencies deriving therefrom. These are simultaneously employed for the drive of the heat source, so that the actual tuning of the heat source over the frequency is no longer implemented, a significant time-savings deriving therefrom.

Further developments can be derived from the subclaims.

In particular, a light-emitting diode (LED) or a laser diode can be advantageously utilized as heat source since they can be electrically amplitude-modulated. Fundamentally, all heat sources can be utilized that offer the possibility of an electrical modulation such that a multi-frequency excitation can be implemented.

When a specific layer sequence is present at the surface of a specimen, then a subject-related setting of the drive frequencies can be advantageously undertaken at the heat source. The relationship applies that an increasing penetration depth into the layer structure accompanies dropping modulation frequency at the heat source. The selection of the drive frequencies can be advantageously set in conformity with a known layer structure.

The target quantities, for example individual layer thicknesses, can be numerically determined with the approach of a regression analysis with non-linear formulation functions or, respectively, with a trainable neural network. Experimental or theoretical/analytical supporting values can thereby be employed as calibration values.

Further advantageous developments can be derived from the subclaims.

Further exemplary embodiments are described below on the basis of schematic Figures.

The measuring time is drastically shortened as a result of the simultaneous multi-frequency excitation and simultaneous parallel interpretation in view of the various frequencies or, respectively, the different, reflected, corresponding infrared radiation. As a result of a suitable selection of the individual frequency parts, the frequency range of measurement in which the heat source is driven can thereby be exactly matched to the measurement problem. The simultaneous intensity modulation with two or more discrete frequencies onto an electrically modulatable heat source enables the parallel interpretation in a corresponding plurality of lock-in amplifiers. Instead, the signal interpretation can also ensue with a FFT or similar digital evaluation method such as correlation or fitting to a sine function upon utilization of a digital oscilloscope.

A hot light source such as, for example, a laser diode or an LED is usually employed as heat source. Either regression analysis or a neural network can be utilized for evaluation following a corresponding plurality of lock-in amplifiers or a fast Fourier transformation.

The critical feature of the invention is comprised in the simultaneity with which a heat source is driven with different frequencies. When, for example, three frequencies have been selected, then their sum supplies an analog signal with which the heat source is modulated. Corresponding evaluation is carried out for each frequency at the evaluation side. This occurs simultaneously.

Figure 1:
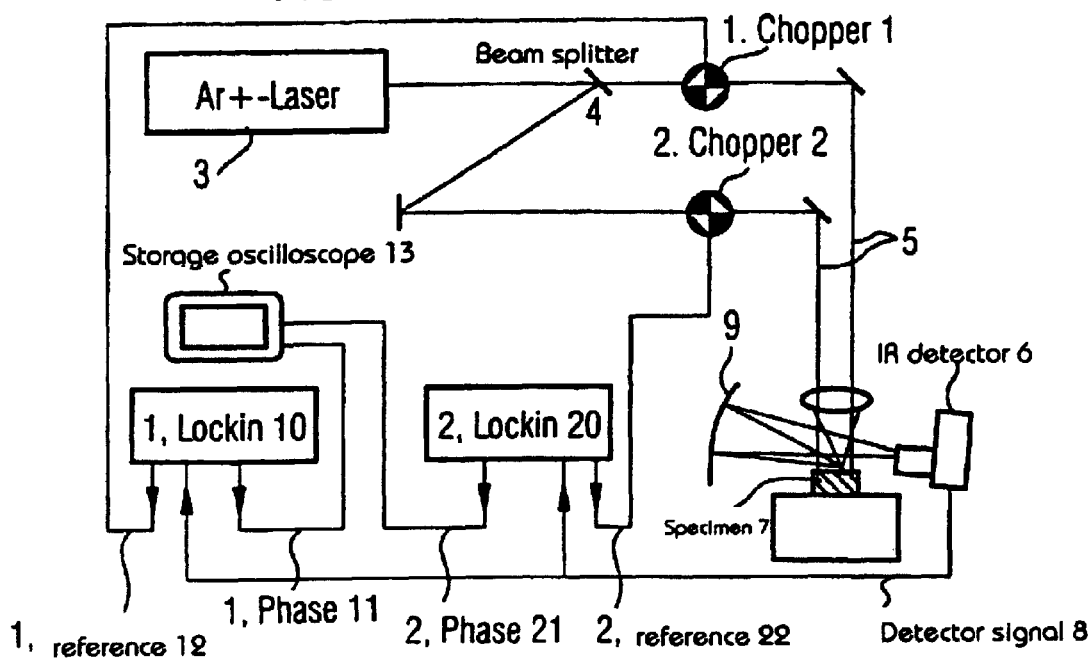
FIG. 1 shows a test setup for the implementation of a method according to the invention.
Figure 2:
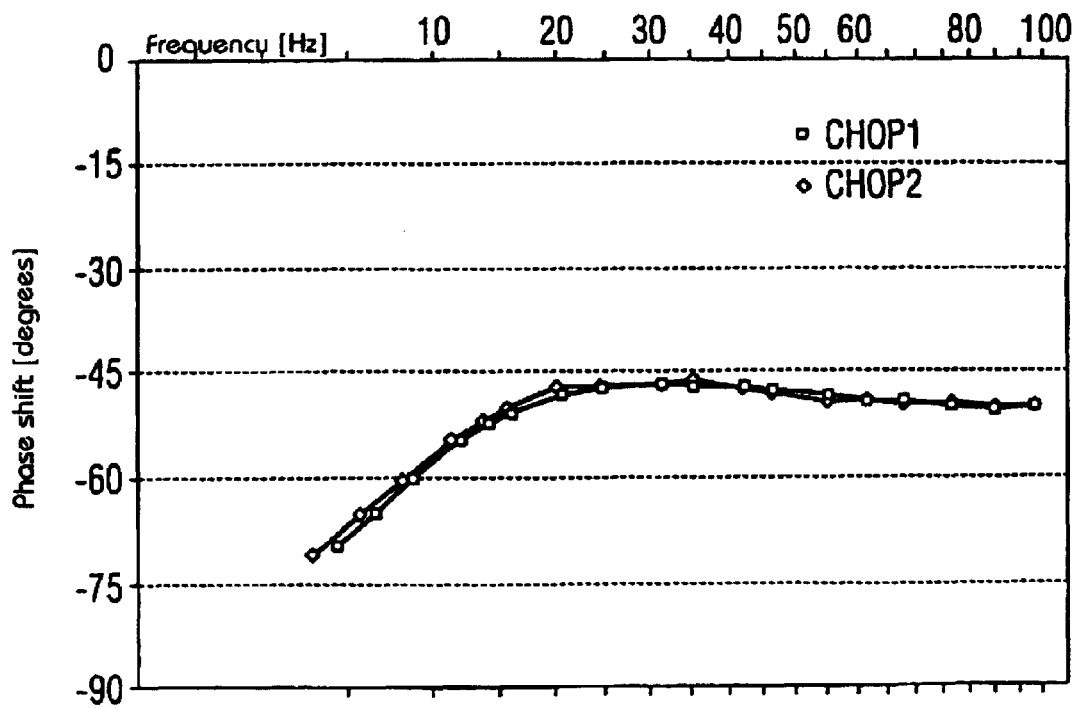
FIG. 2 shows the phase shift of reflected heat waves dependent on the drive frequency of a heat source.

In a test setup corresponding to FIG. 1, a standard specimen that is composed of a TiN layer on a glass lamina is measured. A heat ray output by a laser 3 thereby heats the specimen by regions. The heat ray is divided after exiting the laser, whereby each of the two rays is supplied to a mechanical chopper 1, 2. When passing through the choppers 1, 2, the two rays are modulated with different modulation frequencies f1, f2 and are subsequently focused in common and directed onto the specimen 7. As a result thereof, it is also possible with mechanical modulation to simultaneously excite the specimen with two modulation frequencies. An electronic processing of the various frequencies is advantageous. After the detector signal 8 has been forwarded to two different lock-in amplifiers 10, 20, two phases 11, 21 that can be displayed on a storage oscilloscope 13 are correspondingly obtained as result. The respective reference input 12, 21 of the lock-in amplifiers 10, 20 is occupied with the modulation frequency of the choppers 1 or, respectively, 2. In order to adapt the two beam paths to one another, a phase-frequency curve is first registered, i.e. the frequency of both choppers 1, 2 is simultaneously tuned. The result is shown in FIG. 2. It can be seen in FIG. 2 that the frequency shift arises at approximately −45° with higher frequencies of more than approximately 20 Hz. This is true both for chopper 1 and for chopper 2.

Figure 3:
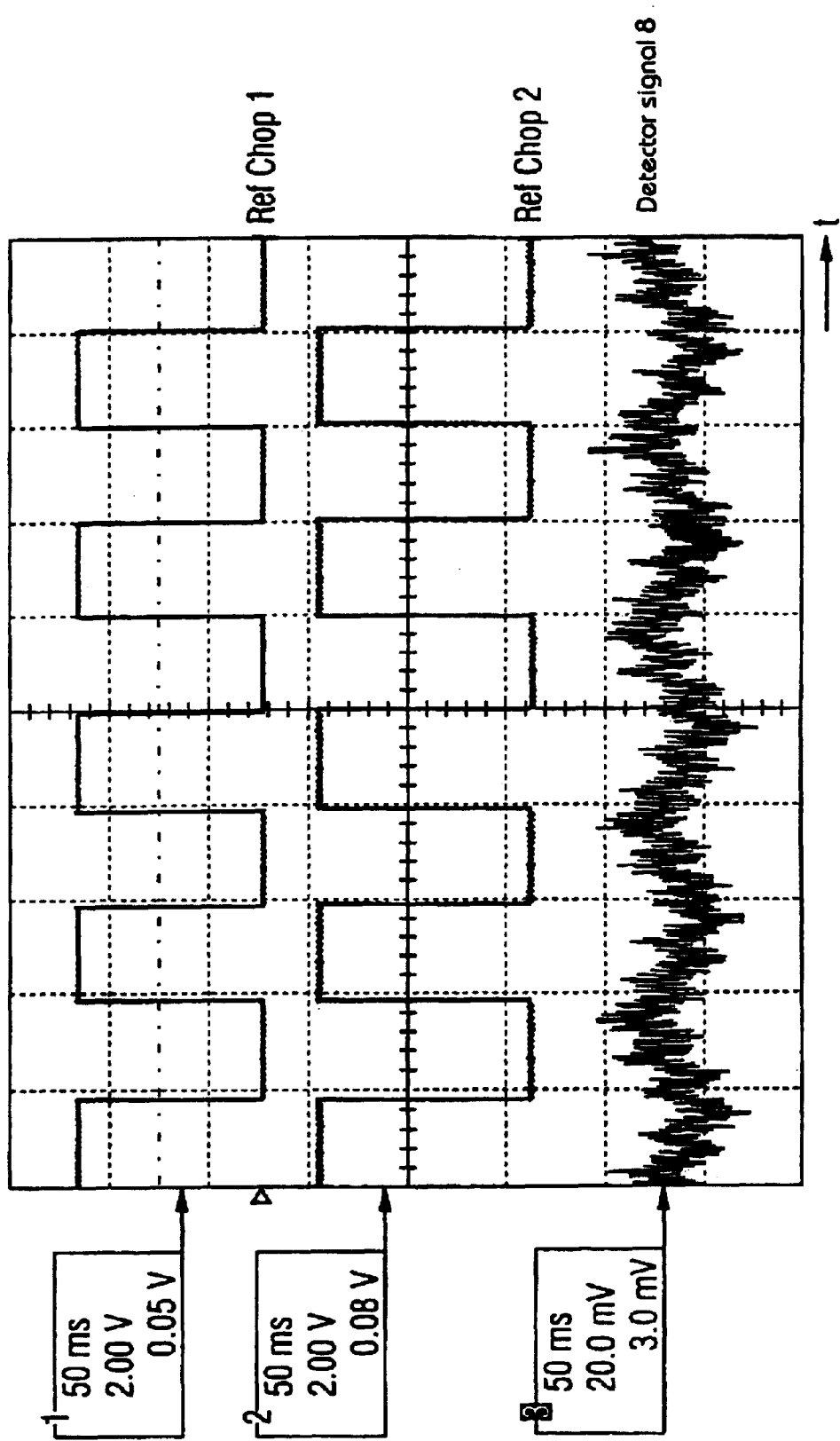
FIG. 3 shows reference and detector signal given a modulation of 10 Hz for two frequency generators (choppers)

FIG. 3 shows the results when both choppers 1, 2 are permanently set to 10 Hz and the detector signal 8 is measured. A frame with three particulars is respectively shown in the illustrations of FIGS. 3–6 to the left next to each signal curve. The first two particulars therein denote the scaling on the axes of the storage oscilloscope. The first values states how many milliseconds between two markings in a box on the abscissa, on which the time is entered, denote [sic]. The second value states how many volts on the ordinate, on which the voltage is entered, the distance between two markings or, respectively, in a box amounts to. The third value represents the actual result, namely a specific voltage that, counted in volts or millivolts, can be converted, for example for an amplitude signal or a phase signal.

Figure 4:
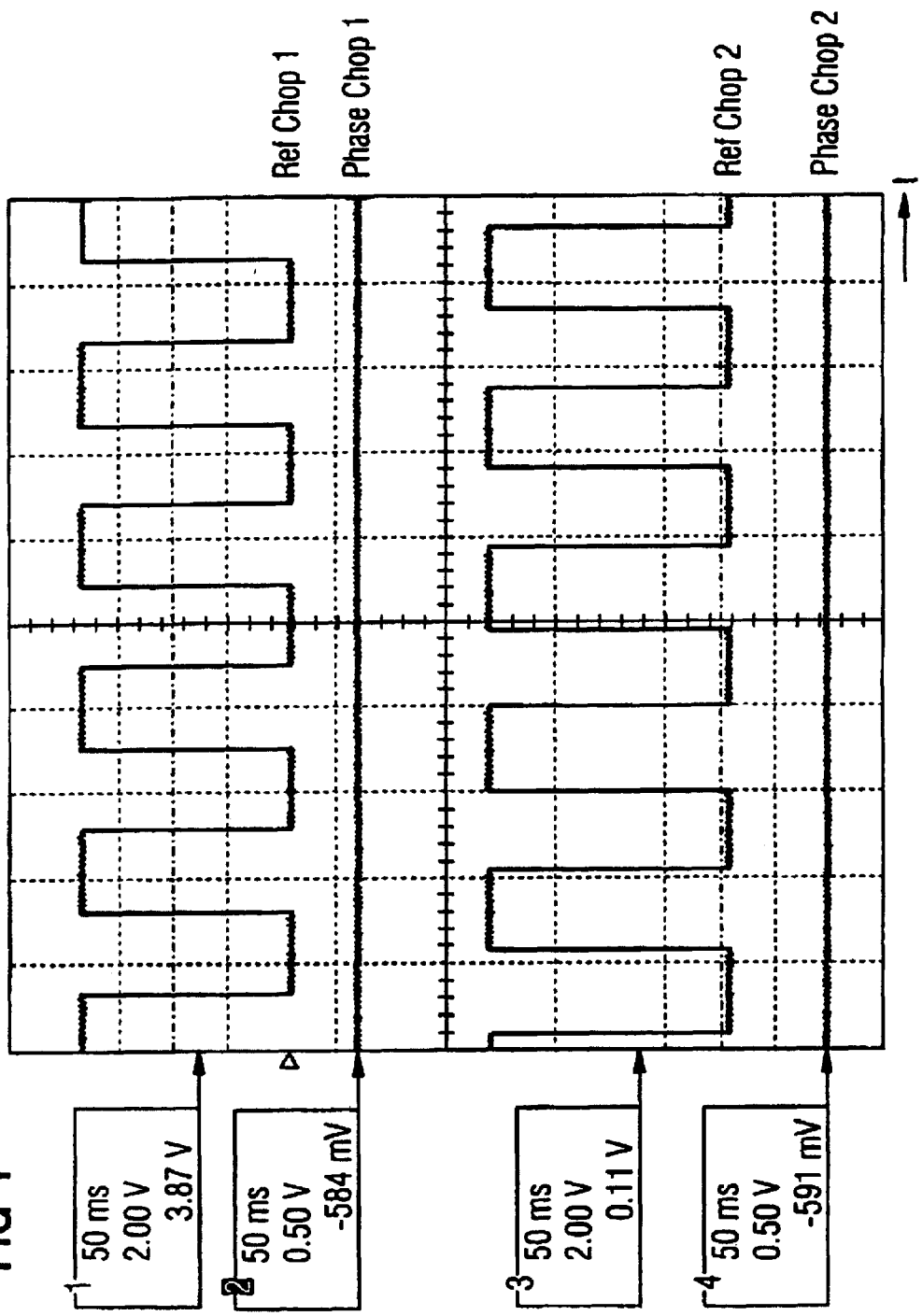
FIG. 4 shows reference and phase signal given a modulation of 10 Hz for both choppers 1, 2.

Measured values for reference, phase and detector signal given a 10 Hz modulation of both choppers 1, 2 are respectively shown on FIGS. 3 and 4. The same presentations as in FIGS. 3 and 4 are employed in FIGS. 5 and 6, whereby, however, the modulation of the first chopper 1 amounts to 40 Hz and that of the second chopper 2 amounts to 20 Hz.

The basis of the illustrated measured values and results according to FIG. 4 contain [sic] that both choppers are permanently set to 10 Hz, and that the detector signal 8 is measured. The uppermost curve at the right represents the curve of the pulse sequence at the chopper 1. A complete oscillation thereby requires the length of two boxes or, respectively, twice 50 ms, so that a frequency of 10 Hz is present here. The same is true of the middle curve, which is present at the second chopper 2. The lowest curve represents the detector signal 8, which is an analog signal at first. In all three instances, the amplitude of the signal is respectively entered as third value in the juxtaposed frame, whereby this [sic], however, are selectable trial parameters.

FIG. 2 shows both the reference as well as the phase given a modulation of 10 Hz for both choppers 1, 2. The pulse frequency is identical to the frequency in FIG. 3. The phase position of the choppers 1, 2 is nearly identical to −584 mV and −591 mV which, when converted, approximately corresponds to a phase shift of 60°. What thereby forms the basis is that 10 mV stands for 1° phase shift. Expressed in other words, the infrared wave or, respectively, heat wave reflected back from the specimen 7 has a phase position that lags behind the phase of the laser signal by 60°.

Figure 5:
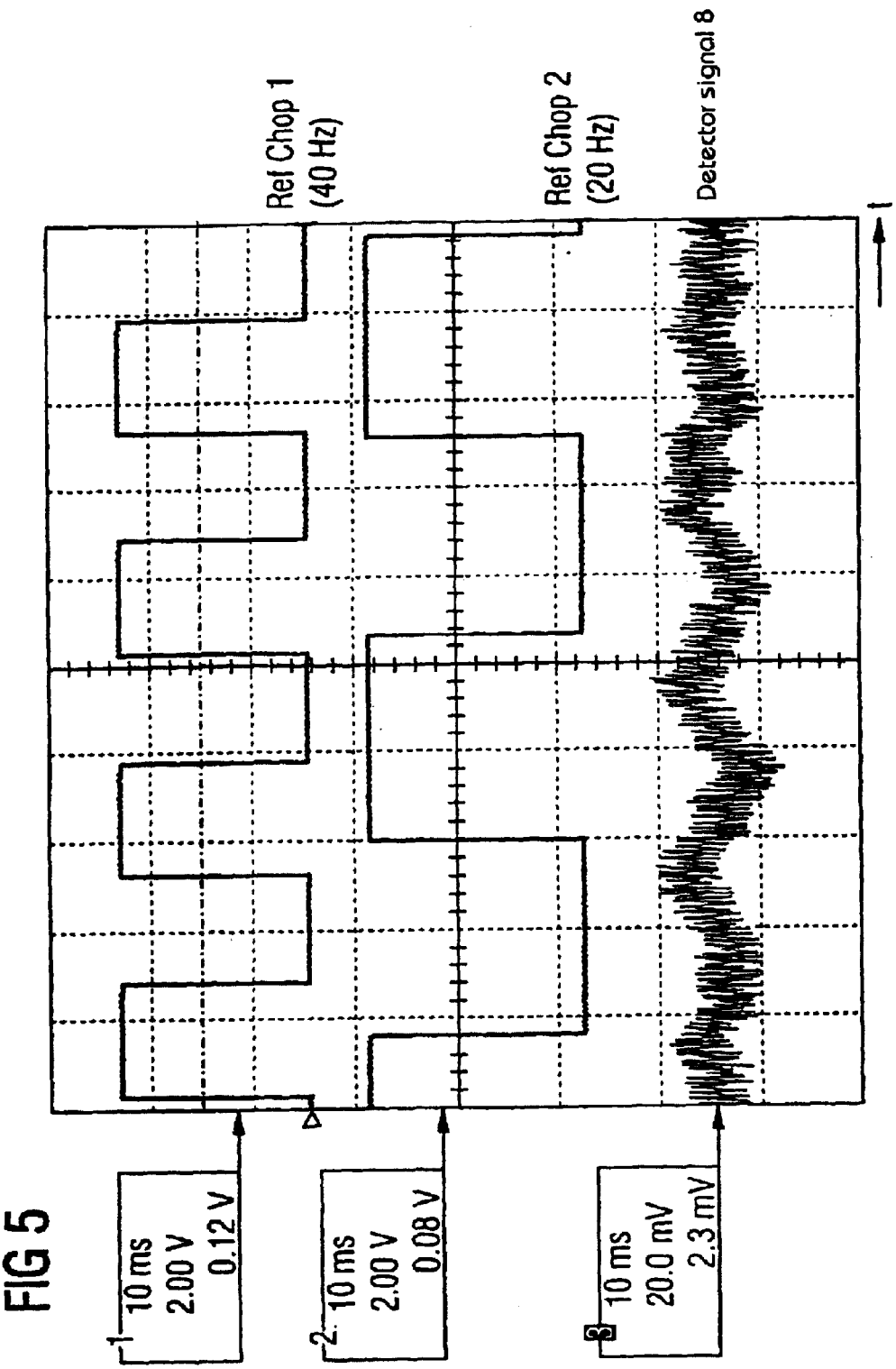
FIG. 5 shows reference and detector signal given a modulation of 40 and 20 Hz.
Figure 6:
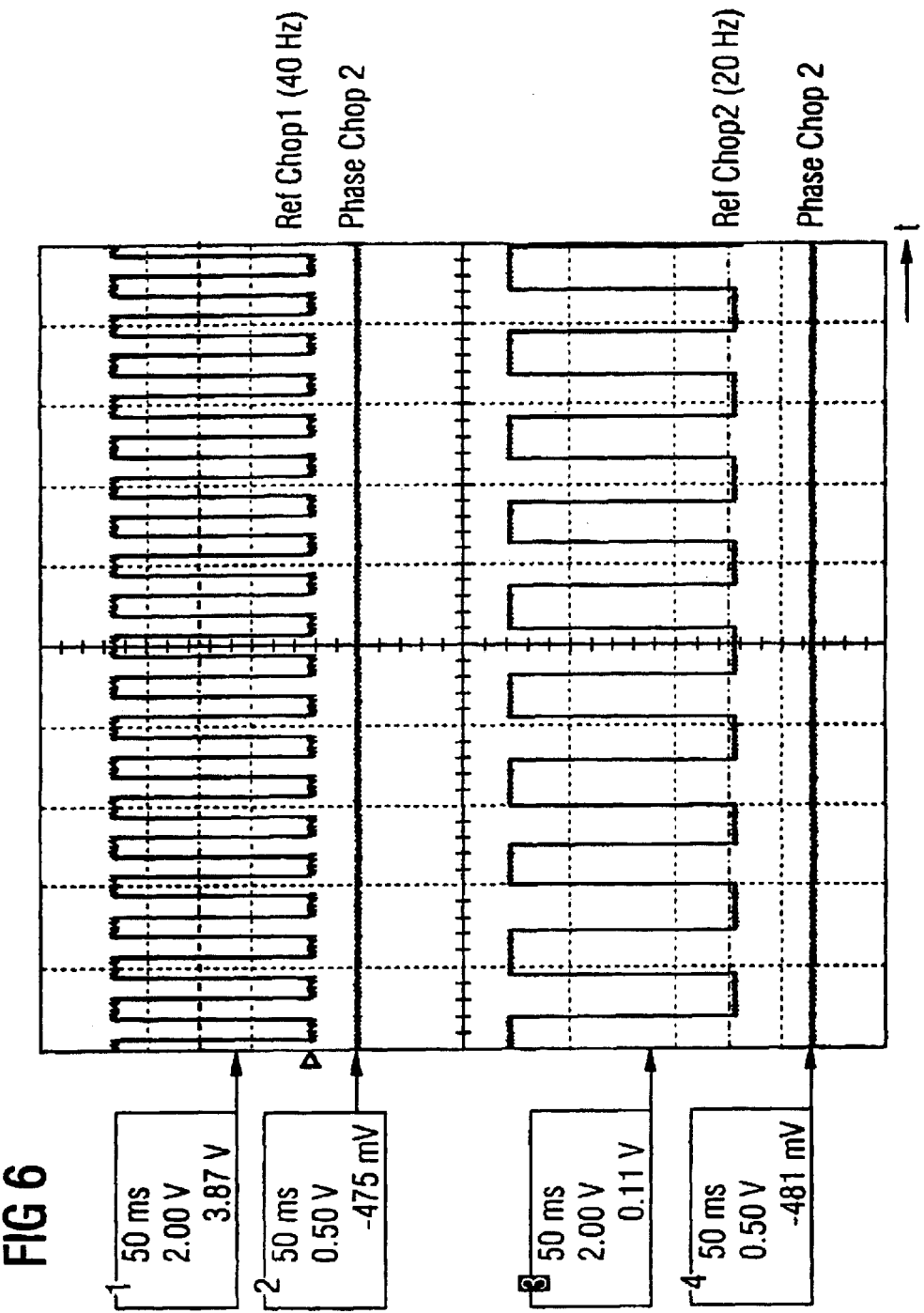
FIG. 6 shows reference and phase signal given a modulation of 40 and 20 Hz.

FIGS. 5 and 6 show signals corresponding to FIGS. 3 and 4. This time, however, the first and second chopper 1, 2 are modulated on different frequencies. The first chopper 1 respectively comprises a pulse frequency of 40 Hz, and the second chopper 2 comprises a pulse frequency of 20 Hz. The detector signal 8 is again a result signal superimposed of a plurality of signals that is converted via the signal processing applied in the method. Corresponding to the second and fourth signal in FIG. 6, the phase position for the two drive frequencies is also approximately the same for the case illustrated in FIGS. 5 and 6.

It can thus be documented by the measurements that it is possible to also correctly obtain the phase when the specimen is simultaneously modulated with two different frequencies instead of tuning the modulation frequency (chirp) as hitherto.

The measurement with the described mechanical choppers represents only one embodiment, whereby the modulation of laser diodes or, respectively, of LEDs with a plurality of frequencies simultaneously is planned. Over and above this, the planar illumination of the specimen 8 can be optimized with appropriate devices, as can the image registration with a camera arrangement. The basis thereby continues to be formed by the principle that the measuring time is shortened by simultaneous multi-frequency excitation and by simultaneous parallel evaluation of the different frequencies.

When it is required to simultaneously determine the geometrical and thermal parameters of a multi-layer structure, then this may not be possible with traditional calculating methods. An analytical formula for the phase dependent on the thermal and geometrical parameters as well as on the modulation frequency can be specified. When, however, this is to be solved for the quantities characterizing the multi-layer structure, then this is not possible analytically. This means that there is an "inverse problem". The interpretation can then ensue on the basis of numerical methods such as, for example, regression analysis or with a neural network, which represents and automation of the determination of the material parameters and involves a higher precision and a time-savings. Moreover, the possibility is opened up of theoretically describing arbitrary layer structures to be photothermally measured and of determining their thermal and geometrical properties.

What is claimed is:

1. A thermal wave measuring method for contact-free measurement of geometrical or thermal features of a layer structure, comprising the steps of:

simultaneously driving a modulatable heat source with at least two predetermined discrete and differently modulated frequencies, thereby periodically heating said layer structure;

receiving infrared radiation emitted by said layer structure that is correspondingly modulated in intensity; and evaluating said receiving infrared radiation as a function of a drive frequency on the basis of amplitude or phase by simultaneously interpreting corresponding drive frequencies.

2. The method according to claim 1, wherein said heat source is a laser, a laser diode, or a light-emitting diode.

3. The method according to claim 1, further comprising the step of:

adapting discrete frequency parts of said drive frequencies to a measurement function.

4. The method according to claim 1, further comprising the step of:

detecting predetermined frequencies with a lock-in evaluation.

5. The method according to claim 4:

further comprising the step of providing an additional evaluation based on a regression analysis or a neural network.

6. The method according to claim 1, further comprising the step of:

evaluating individual frequencies using a Fast Fourier Transform.

7. The method according to claim 6:

further comprising the step of providing an additional evaluation based on a regression analysis or a neural network.

8. The method according to claim 1, further comprising the step of:

calibrating said method to a specific layer structure utilizing mathematically specific, theoretical values as well as utilizing experimentally supported data.

9. The method according to claim 1, further comprising the step of:

determining geometrical features given known thermal features of the layer structure.

10. The method according to claim 1, further comprising the step of:

determining thermal features given known geometrical features of the layer structure.

* * * * *